US011759341B2

(12) United States Patent
Gilmartin et al.

(10) Patent No.: US 11,759,341 B2
(45) Date of Patent: Sep. 19, 2023

(54) ANTI-MIGRATION STENT

(71) Applicant: BOSTON SCIENTIFIC SCIMED, INC., Maple Grove, MN (US)

(72) Inventors: Gary Gilmartin, Foxford (IE); Louis McNern, Donegal (IE); Michael Walsh, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 147 days.

(21) Appl. No.: 17/125,116

(22) Filed: Dec. 17, 2020

(65) Prior Publication Data
US 2021/0212848 A1    Jul. 15, 2021

Related U.S. Application Data

(60) Provisional application No. 62/960,470, filed on Jan. 13, 2020.

(51) Int. Cl.
*A61F 2/90* (2013.01)
*A61F 2/86* (2013.01)
*A61F 2/82* (2013.01)
*A61F 2/848* (2013.01)

(52) U.S. Cl.
CPC .................. *A61F 2/90* (2013.01); *A61F 2/82* (2013.01); *A61F 2/848* (2013.01); *A61F 2002/825* (2013.01)

(58) Field of Classification Search
CPC ...... A61F 2/04; A61F 2/07; A61F 2/82; A61F 2/90; A61F 2/848; A61F 2002/825; A61F 2230/0086; A61F 2250/0058
See application file for complete search history.

(56) References Cited

U.S. PATENT DOCUMENTS

| 4,994,071 A | 2/1991 | MacGregor |
| 5,591,197 A | 1/1997 | Orth et al. |
| 5,674,277 A | 10/1997 | Freitag |
| 5,681,346 A | 10/1997 | Orth et al. |

(Continued)

FOREIGN PATENT DOCUMENTS

| EP | 0732088 A2 | 9/1996 |
| EP | 0732089 A2 | 9/1996 |

(Continued)

OTHER PUBLICATIONS

International Search Report and Written Opinion dated Jun. 4, 2021 for International Application No. PCT/US2020/065583.

*Primary Examiner* — Dinah Baria
(74) *Attorney, Agent, or Firm* — Seager, Tufte & Wickhem, LLP

(57) ABSTRACT

An illustrative stent includes an elongated tubular member comprising at least one strut or filament forming a tubular wall having a plurality of cells extending through a thickness of the tubular wall. The elongated tubular member may be configured to move between a radially collapsed configuration and a radially expanded configuration. A coating is disposed on the elongated tubular member and spanning the plurality of cells. The coating forms a pocket within at least some of the cells of the plurality of cells and extends radially inward of the tubular wall to define a void. In some instances, a partition or wall is positioned within at least some of the pockets and transects the void.

18 Claims, 10 Drawing Sheets

(56) References Cited

U.S. PATENT DOCUMENTS

| | | |
|---|---|---|
| 5,800,526 A | 9/1998 | Anderson et al. |
| 5,814,063 A | 9/1998 | Freitag |
| 6,027,526 A | 2/2000 | Limon et al. |
| 6,210,429 B1 | 4/2001 | Vardi et al. |
| 6,443,972 B1 | 9/2002 | Bosma et al. |
| 6,506,437 B1 | 1/2003 | Harish et al. |
| 7,060,089 B2 | 6/2006 | Ley et al. |
| 7,527,644 B2 | 5/2009 | Mangiardi et al. |
| 7,547,321 B2 | 6/2009 | Silvestri et al. |
| 7,604,660 B2 | 10/2009 | Borg et al. |
| 7,608,099 B2 | 10/2009 | Johnson et al. |
| 7,637,934 B2 | 12/2009 | Mangiardi et al. |
| 7,637,942 B2 | 12/2009 | Mangiardi et al. |
| 7,651,520 B2 | 1/2010 | Fischell et al. |
| 7,731,654 B2 | 6/2010 | Mangiardi et al. |
| 7,740,791 B2 | 6/2010 | Kleine et al. |
| 7,785,360 B2 | 8/2010 | Freitag |
| 7,803,180 B2 | 9/2010 | Burpee et al. |
| 7,806,918 B2 | 10/2010 | Nissl et al. |
| 7,815,673 B2 | 10/2010 | Bloom et al. |
| 7,875,068 B2 | 1/2011 | Mangiardi et al. |
| 7,887,579 B2 | 2/2011 | Mangiardi et al. |
| 7,942,921 B2 | 5/2011 | Nissl et al. |
| 7,959,671 B2 | 6/2011 | Mangiardi et al. |
| 8,080,053 B2 | 12/2011 | Satasiya et al. |
| 8,128,679 B2 | 3/2012 | Casey |
| 8,142,488 B2 | 3/2012 | Reynolds et al. |
| 8,206,436 B2 | 6/2012 | Mangiardi et al. |
| 8,262,721 B2 | 9/2012 | Welborn et al. |
| 8,267,987 B2 | 9/2012 | Johnson et al. |
| 8,298,277 B2 | 10/2012 | Mangiardi et al. |
| 8,323,350 B2 | 12/2012 | Nissl |
| 8,353,946 B2 | 1/2013 | Mangiardi et al. |
| 8,535,366 B2 | 9/2013 | Mangiardi et al. |
| 8,652,196 B2 | 2/2014 | Nissl |
| 8,834,558 B2 | 9/2014 | Nissl |
| 8,926,683 B2 | 1/2015 | Gill et al. |
| 9,539,126 B2 | 1/2017 | Walsh et al. |
| 10,219,921 B2 | 3/2019 | Harris et al. |
| 2002/0179166 A1 | 12/2002 | Houston et al. |
| 2005/0131515 A1 | 6/2005 | Cully et al. |
| 2005/0163954 A1 | 7/2005 | Shaw |
| 2006/0036311 A1 | 2/2006 | Nakayama et al. |
| 2006/0281966 A1 | 12/2006 | Peacock, III et al. |
| 2007/0005127 A1 | 1/2007 | Boekstegers et al. |
| 2007/0061005 A1 | 3/2007 | Kim et al. |
| 2007/0123969 A1 | 5/2007 | Gianotti |
| 2007/0213810 A1 | 9/2007 | Newhauser et al. |
| 2008/0319540 A1 | 12/2008 | Jordan et al. |
| 2009/0187240 A1 | 7/2009 | Clerc et al. |
| 2009/0248132 A1 | 10/2009 | Bloom et al. |
| 2010/0030321 A1 | 2/2010 | Mach |
| 2010/0100170 A1 | 4/2010 | Tan et al. |
| 2010/0256731 A1 | 10/2010 | Mangiardi |
| 2010/0286760 A1 | 11/2010 | Beach et al. |
| 2011/0230957 A1 | 9/2011 | Bonsignore et al. |
| 2012/0150277 A1 | 6/2012 | Wood et al. |
| 2012/0310363 A1 | 12/2012 | Gill et al. |
| 2013/0018215 A1 | 1/2013 | Snider et al. |
| 2013/0018452 A1 | 1/2013 | Weitzner et al. |
| 2013/0085565 A1 | 4/2013 | Eller et al. |
| 2013/0103162 A1 | 4/2013 | Costello |
| 2013/0103163 A1 | 4/2013 | Krimsky et al. |
| 2013/0110253 A1 | 5/2013 | Gill et al. |
| 2013/0116770 A1 | 5/2013 | Robinson |
| 2013/0116771 A1 | 5/2013 | Robinson |
| 2013/0116772 A1 | 5/2013 | Robinson |
| 2013/0123897 A1 | 5/2013 | Robinson |
| 2013/0172983 A1 | 7/2013 | Clerc et al. |
| 2013/0184808 A1 | 7/2013 | Hall et al. |
| 2013/0184810 A1 | 7/2013 | Hall et al. |
| 2013/0325141 A1 | 12/2013 | Gill et al. |
| 2014/0067047 A1 | 3/2014 | Eller et al. |
| 2014/0079758 A1 | 3/2014 | Hall et al. |
| 2014/0081414 A1 | 3/2014 | Hall et al. |
| 2014/0086971 A1 | 3/2014 | Hall et al. |
| 2014/0248418 A1 | 9/2014 | Eller et al. |
| 2014/0249619 A1 | 9/2014 | Eller et al. |
| 2014/0257461 A1 | 9/2014 | Robinson et al. |
| 2014/0277562 A1 | 9/2014 | Seddon et al. |
| 2014/0277573 A1 | 9/2014 | Gill et al. |
| 2015/0045908 A1 | 2/2015 | McMahon |
| 2015/0051693 A1* | 2/2015 | Bertolino ............... B29C 65/48 623/1.13 |
| 2015/0073529 A1 | 3/2015 | Fleury et al. |
| 2015/0148887 A1 | 5/2015 | Beach et al. |
| 2016/0256296 A1 | 9/2016 | Rubesch et al. |

FOREIGN PATENT DOCUMENTS

| | | |
|---|---|---|
| EP | 1776066 B1 | 2/2012 |
| EP | 2702964 A1 | 3/2014 |
| JP | 2011509758 A | 3/2011 |
| JP | 2019516504 A | 6/2019 |
| WO | 2005112821 A2 | 12/2005 |
| WO | 2010124286 A1 | 10/2010 |
| WO | 2012047308 A1 | 4/2012 |
| WO | 2014010679 A1 | 1/2014 |

* cited by examiner

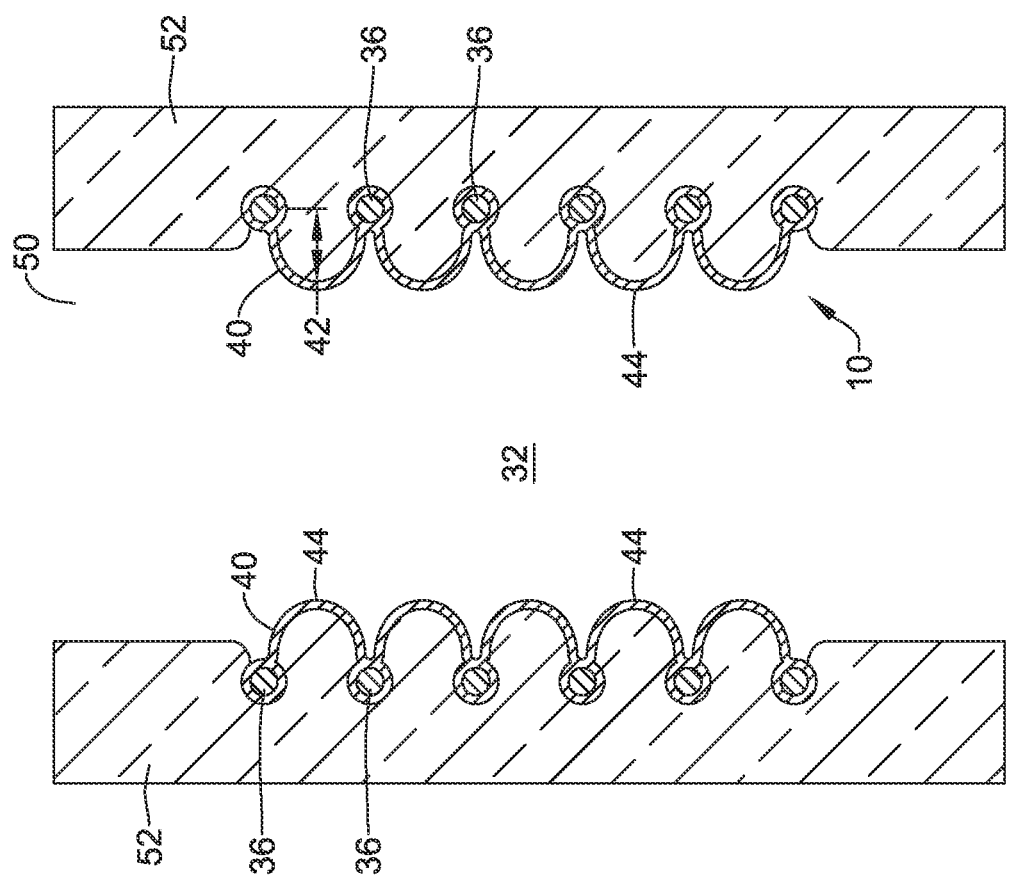

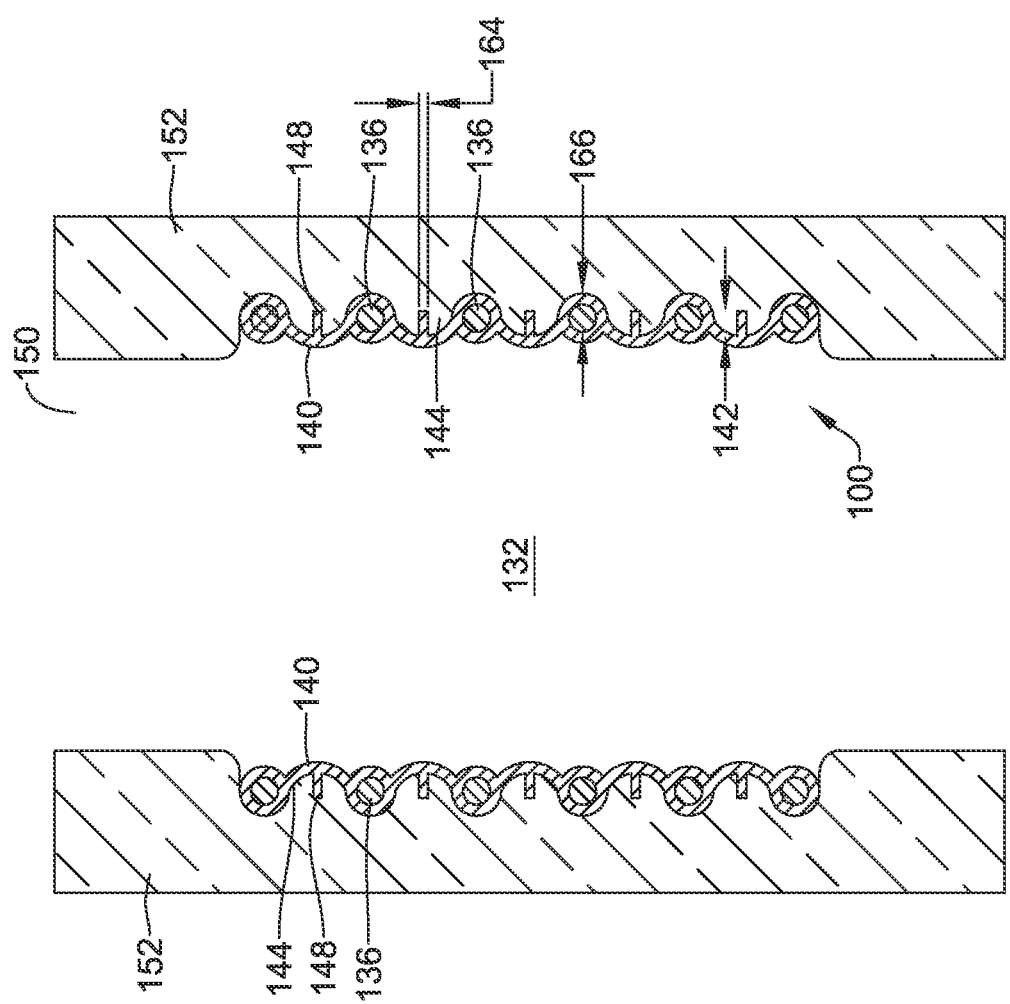

ANTI-MIGRATION STENT

CROSS REFERENCE TO RELATED APPLICATIONS

The present application claims the benefit of and priority to U.S. Provisional Patent Application Ser. No. 62/960,470, filed on Jan. 13, 2020, the disclosure of which is incorporated herein by reference.

TECHNICAL FIELD

The present disclosure pertains to medical devices, methods for manufacturing medical devices, and uses thereof. More particularly, the present disclosure pertains to an anti-migration stent for implantation in a body lumen, and associated methods.

BACKGROUND

Implantable stents are devices that are placed in a body lumen, such as the esophageal tract, the gastrointestinal tract (including the intestine, stomach and the colon), tracheobronchial tract, urinary tract, biliary tract, vascular system, etc. to provide support and to maintain the body lumen open. These stents are manufactured by any one of a variety of different manufacturing methods and may be used according to any one of a variety of methods. Of the known stents, delivery systems, and methods, each has certain advantages and disadvantages. For example, in some stents, the compressible and flexible properties that assist in stent delivery may also result in a stent that has a tendency to migrate from its originally deployed position. For example, stents that are designed to be positioned in the esophageal or gastrointestinal tract may have a tendency to migrate due to peristalsis (i.e., the involuntary constriction and relaxation of the muscles of the esophagus, intestine, and colon which push the contents of the canal therethrough). Thus, there is an ongoing need to provide alternative stents having anti-migration features and associated delivery systems as well as alternative methods for manufacturing and using stents having anti-migration features and associated delivery systems.

BRIEF SUMMARY

This disclosure provides design, material, manufacturing method, and use alternatives for medical devices. An example medical device may include a stent.

In a first example, a stent may comprise an elongated tubular member comprising at least one strut forming a tubular wall having a plurality of cells extending through a thickness of the tubular wall, the elongated tubular member configured to move between a radially collapsed configuration and a radially expanded configuration, a coating disposed on the elongated tubular member and spanning the plurality of cells, the coating forming a pocket within at least some of the plurality of cells and extending radially inward of the tubular wall to define a void, and a partition positioned within at least some of the pockets, each partition extending radially outward from a bottom surface of the pocket and transecting the void.

Alternatively or additionally to any of the examples above, in another example, at least some of the partitions may extend generally perpendicular to a central longitudinal axis of the elongated tubular member.

Alternatively or additionally to any of the examples above, in another example, at least some of the partitions may extend generally parallel to a central longitudinal axis of the elongated tubular member.

Alternatively or additionally to any of the examples above, in another example, at least some of the partitions may extend at an oblique angle relative to a central longitudinal axis of the elongated tubular member.

Alternatively or additionally to any of the examples above, in another example, a height of the partitions may be approximately equal to a height of the at least one strut having the coating disposed thereon.

Alternatively or additionally to any of the examples above, in another example, the at least one strut may form a plurality of cross-over points.

Alternatively or additionally to any of the examples above, in another example, at least some of the partitions may extend between adjacent cross-over points.

Alternatively or additionally to any of the examples above, in another example, at least some of the partitions may extend from a first side of the pocket to a second side of the pocket in which it is positioned.

Alternatively or additionally to any of the examples above, in another example, at least one pocket may include two or more partitions.

Alternatively or additionally to any of the examples above, in another example, the coating may define an entirety of a surface of a lumen extending longitudinally through the stent.

Alternatively or additionally to any of the examples above, in another example, at least some of the pockets may include an aperture formed therethrough.

Alternatively or additionally to any of the examples above, in another example, the coating and the partitions may be formed as a single monolithic structure.

Alternatively or additionally to any of the examples above, in another example, the coating may be disposed over an inner surface and/or an outer surface of the elongated tubular member.

In another example, a stent may comprise an elongated tubular member comprising at least one strut forming a tubular wall having a plurality of cells extending through a thickness of the tubular wall, the elongated tubular member configured to move between a radially collapsed configuration and a radially expanded configuration and a coating disposed on the elongated tubular member and spanning the plurality of cells, the coating forming a pocket within at least some of the plurality of cells and extending radially inward of the tubular wall to define a void. The pockets may be pyramidal shaped, with four converging side walls and a base wall intersecting each of the four converging side walls.

Alternatively or additionally to any of the examples above, in another example, the stent may further comprise a partition positioned within at least some of the pockets, each partition extending radially outward from the base surface of the pocket and transecting the void.

In another example, a stent may comprise an elongated tubular member comprising at least one interwoven filament forming a tubular wall, the at least one interwoven filament forming a plurality of cross-over points and defining a plurality of cells therebetween extending through a thickness of the tubular wall, the elongated tubular member configured to move between a radially collapsed configuration and a radially expanded configuration, a polymer coating disposed on the elongated tubular member, the coating forming a pocket within at least some of the plurality of cells and extending radially inward of the tubular wall to define a void, and a partition formed within at least some of the pockets, each partition extending radially outward from a bottom surface of the pocket and transecting the void between opposing cross-over points of the at least one strut forming the cell in which the pocket is positioned.

Alternatively or additionally to any of the examples above, in another example, at least some of the partitions may extend generally perpendicular to a central longitudinal axis of the elongated tubular member.

Alternatively or additionally to any of the examples above, in another example, at least some of the partitions may extend generally parallel to a central longitudinal axis of the elongated tubular member.

Alternatively or additionally to any of the examples above, in another example, the coating may define an entirety of a surface of a lumen extending longitudinally through the stent.

Alternatively or additionally to any of the examples above, in another example, the coating and the partitions may be formed as a single monolithic structure.

Alternatively or additionally to any of the examples above, in another example, a radial outermost extent of the partitions may be located flush with or radially inward of an outer surface of the tubular wall.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments in connection with the accompanying drawings, in which:

FIG. 3A is a cross-sectional view of an alternative variation of the stent of FIG. 1 disposed within a body lumen.

FIG. 6A is a cross-sectional view of an alternative variation of the stent of FIG. 4 disposed within a body lumen.

Figure 1:
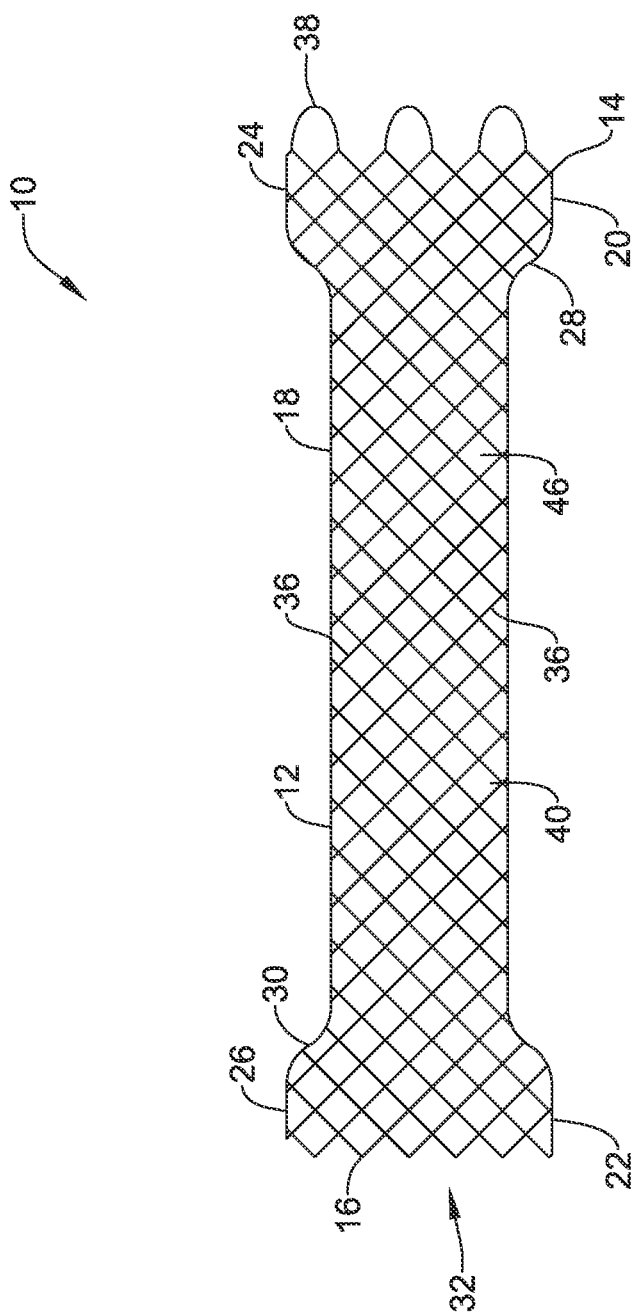
FIG. 1 is a side view of an illustrative stent having an anti-migration system.

While the disclosure is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

In some instances, it may be desirable to provide an endoluminal implant, or stent, that can deliver luminal patency in a patient with an esophageal stricture or other medical condition. Such stents may be used in patients experiencing dysphagia, sometimes due to esophageal cancer. An esophageal stent may allow a patient to maintain nutrition via oral intake during cancer treatment or palliation periods. However, a common complication of gastrointestinal (GI) stents is stent migration due to the peristaltic motion subjected to the stent. Uncoated stents allow the granulation tissue of the esophagus to encompass the stent and effectively grip the wires of the stent. While this tissue ingrowth may help prevent the migration of the stent, the stent may be difficult to remove. It may be desirable to provide a stent that can deliver luminal patency while minimizing migration of the stent and allowing for removal of the stent. While the embodiments disclosed herein are discussed with reference to esophageal stents, it is contemplated that the stents described herein may be used and sized for use in other locations such as, but not limited to: bodily tissue, bodily organs, vascular lumens, non-vascular lumens and combinations thereof, such as, but not limited to, in the coronary or peripheral vasculature, trachea, bronchi, colon, small intestine, biliary tract, urinary tract, prostate, brain, stomach and the like.

FIG. 1 illustrates a side view of an illustrative endoluminal implant 10, such as, but not limited to, a stent. In some instances, the stent 10 may be formed from an elongated tubular member 12. While the stent 10 is described as generally tubular, it is contemplated that the stent 10 may take any cross-sectional shape desired. The stent 10 may have a first, or proximal end 14, a second, or distal end 16, and an intermediate region 18 disposed between the first end 14 and the second end 16. The stent 10 may include a lumen 32 extending from a first opening adjacent the first end 14 to a second opening adjacent to the second end 16 to allow for the passage of food, fluids, etc.

The stent 10 may be expandable from a first radially collapsed configuration (not explicitly shown) to a second radially expanded configuration. In some cases, the stent 10 may be deployed to a configuration between the collapsed configuration and a fully expanded configuration. The stent 10 may be structured to extend across a stricture and to apply a radially outward pressure to the stricture in a lumen to open the lumen and allow for the passage of foods, fluids, air, etc.

In some embodiments, the proximal end 14 of the stent 10 may include a plurality of loops 38. The loops 38 may be configured to receive a retrieval tether or suture (not explicitly shown) interwoven therethrough, or otherwise passing through one or more of the loops 38. The retrieval suture may be used to collapse and retrieve the stent 10, if so desired. For example, the retrieval suture may be pulled like a drawstring to radially collapse the proximal end 14 of the stent 10 to facilitate removal of the stent 10 from a body lumen.

The stent 10 may have a woven structure, fabricated from a number of filaments or struts 36 forming a tubular wall. In some embodiments, the stent 10 may be knitted or braided with a single filament or strut interwoven with itself and defining open cells 46 extending through the thickness of the tubular wall of the stent 10. In other embodiments, the stent 10 may be braided with several filaments or struts interwoven together and defining open cells 46 extending along a length and around the circumference of the tubular wall of the stent 10. The open cells 46 may each define an opening from an outer surface of the tubular wall to an inner surface of the tubular wall (e.g., through a thickness thereof) that is free from the filaments or struts 36. Some exemplary stents including braided filaments include the WallFlex®, WALL-STENT®, and Polyflex® stents, made and distributed by Boston Scientific, Corporation. In another embodiment, the stent 10 may be knitted, such as the Ultraflex™ stents made by Boston Scientific, Corporation. In yet another embodiment, the stent 10 may be of a knotted type, such the Precision Colonic™ stents made by Boston Scientific, Corporation. In still another embodiment, the stent 10 may be a laser cut tubular member, such as the EPIC™ stents made by Boston Scientific, Corporation. A laser cut tubular member may have an open and/or closed cell geometry including one or more interconnected monolithic filaments or struts defining open cells 46 therebetween, with the open cells 46 extending along a length and around the circumference of the tubular wall. The open cells 46 may each define an opening from an outer surface of the tubular wall to an inner surface of the tubular wall (e.g., through a thickness thereof) that is free from the interconnected monolithic filaments or struts. In some instances, an inner and/or outer surface of the tubular wall of the stent 10 may be entirely, substantially, or partially, covered with a polymeric covering or coating 40, as will be described in more detail herein. The covering or coating 40 may extend across and/or occlude one or more, or a plurality of the cells 46 defined by the struts or filaments 36. The covering or coating 40 may help reduce food impaction and/or tumor or tissue ingrowth. In some cases, the stent 10 may be a self-expanding stent (SES), although this is not required.

In some instances, in the radially expanded configuration, the stent 10 may include a first end region 20 proximate the proximal end 14 and a second end region 22 proximate the second end 16. In some embodiments, the first end region 20 and the second end region 22 may include retention features or anti-migration flared regions 24, 26 having enlarged diameters relative to the intermediate portion 18. The anti-migration flared regions 24, 26, which may be positioned adjacent to the first end 14 and the second end 16 of the stent 10, may be configured to engage an interior portion of the walls of the esophagus or other body lumen. In some embodiments, the retention features, or flared regions 24, 26 may have a larger diameter than the cylindrical intermediate region 18 of the stent 10 to prevent the stent 10 from migrating once placed in the esophagus or other body lumen. It is contemplated that the transition 28, 30 from the cross-sectional area of the intermediate region 18 to the retention features or flared regions 24, 26 may be gradual, sloped, or occur in an abrupt step-wise manner, as desired.

In some embodiments, the first anti-migration flared region 24 may have a first outer diameter and the second anti-migration flared region 26 may have a second outer diameter. In some instances, the first and second outer diameters may be approximately the same, while in other instances, the first and second outer diameters may be different. In some embodiments, the stent 10 may include only one or none of the anti-migration flared regions 24, 26. For example, the first end region 20 may include an anti-migration flare 24 while the second end region 22 may have an outer diameter similar to the intermediate region 18. It is further contemplated that the second end region 22 may include an anti-migration flare 26 while the first end region 20 may have an outer diameter similar to an outer diameter of the intermediate region 18. In some embodiments, the stent 10 may have a uniform outer diameter from the first end 14 to the second end 16. In some embodiments, the outer diameter of the intermediate region 18 may be in the range of about 15 to 25 millimeters. The outer diameter of the anti-migration flares 24, 26 may be in the range of about 20 to 30 millimeters. It is contemplated that the outer diameter of the stent 10 may be varied to suit the desired application.

It is contemplated that the elongated tubular member of the stent 10 can be made from a number of different materials such as, but not limited to, metals, metal alloys, shape memory alloys and/or polymers, as desired, enabling the stent 10 to be expanded into shape when accurately positioned within the body. In some instances, the material may be selected to enable the stent 10 to be removed with relative ease as well. For example, the elongated tubular member of the stent 10 can be formed from alloys such as, but not limited to, nitinol and Elgiloy®. Depending on the material selected for construction, the stent 10 may be self-expanding or require an external force to expand the stent 10. In some embodiments, composite filaments may be used to make the stent 10, which may include, for example, an outer shell or cladding made of nitinol and a core formed of platinum or other radiopaque material. It is further contemplated the elongated tubular member of the stent 10 may be formed from polymers including, but not limited to, polyethylene terephthalate (PET). In some instances, the filaments of the stent 10, or portions thereof, may be bioabsorbable or biodegradable, while in other instances the filaments of the stent 10, or portions thereof, may be biostable.

Figure 2A:
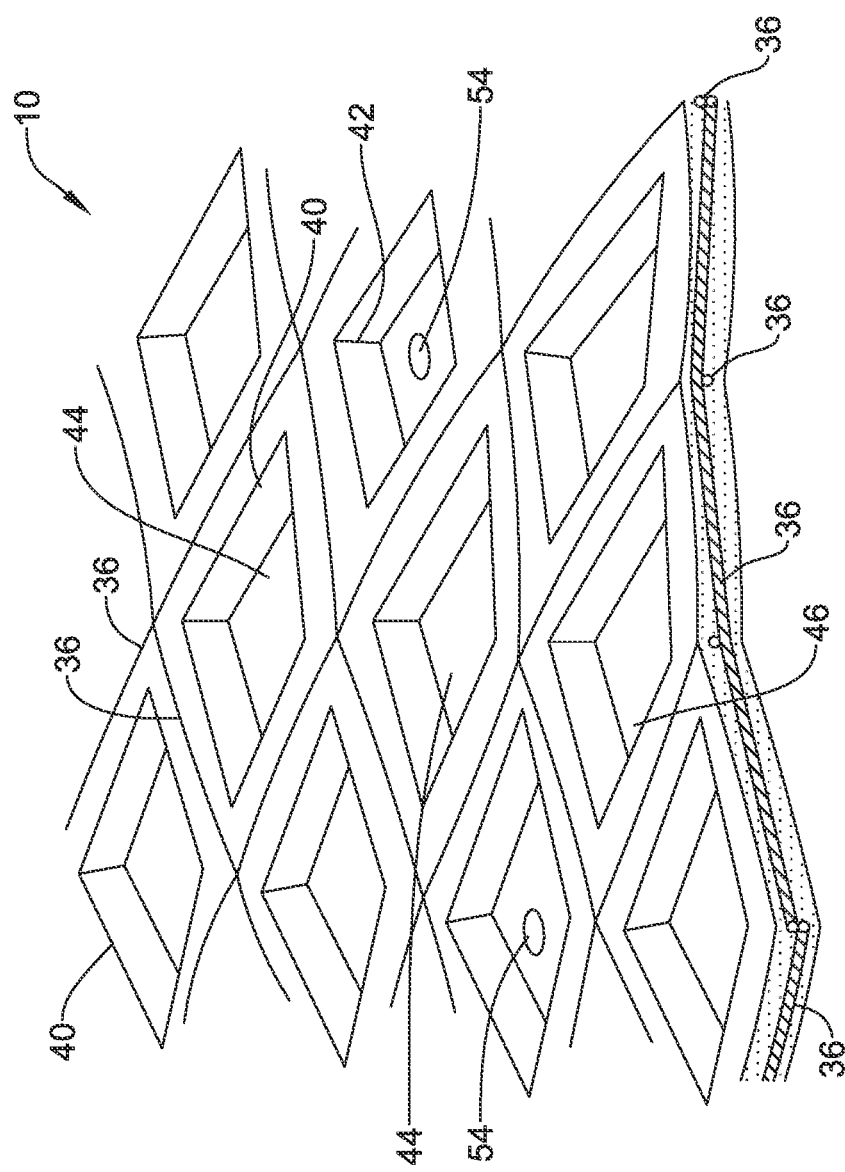
FIG. 2A is a partial perspective view of the illustrative stent of FIG. 1.
Figure 2B:
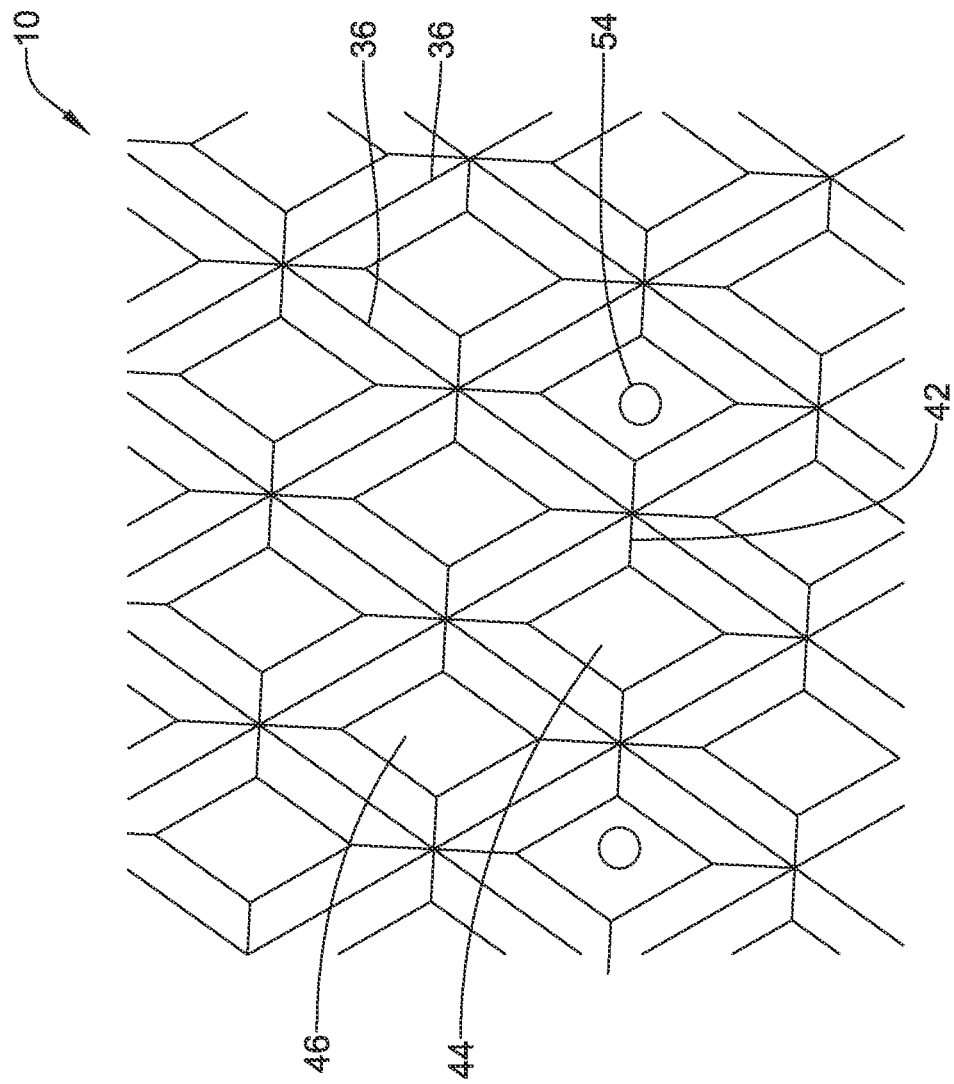
FIG. 2B is a partial side view of the illustrative stent of FIG. 1.

FIG. 2A illustrates a partial perspective view of the illustrative stent 10 of FIG. 1 and FIG. 2B illustrates a partial side view of the illustrative stent 10 of FIG. 1. As described above, the inner and/or outer surface of the tubular wall of the stent 10 may be entirely, substantially, or partially covered with a polymeric covering or coating 40. The coating 40 may be silicone, polyurethane or other flexible polymeric material. The coating 40 may be applied such that there is an excess of material or a pocket of material 44 extending between the struts 36. For example, instead of extending generally taut in the same plane as the struts 36, the coating 40 may be loose and extend radially inward from the struts 36 for a radial distance or height 42 to form a void. In some instances, the pocket 44 may be generally pyramidal shaped, with four flat converging (e.g., angled) side walls and a flat bottom or base wall. While the pocket 44 is generally illustrated as having a rhombus cross-sectional shape similar to a diamond shape of the cells 46 formed by the struts 36, the pocket 44 may take any shape desired. For instance, in some instances the pocket 44 may have a base wall having a generally arcuate shape, such as a generally spherical shape with a spherically concave radially outward facing surface and a spherically convex radially inwardly facing surface. The pocket 44 may form a void between a radially outward surface (e.g., a base surface) of the pocket 44 and the circumference of the tubular wall of the stent 10 formed by the struts 36.

In some instances, the pockets 44 may be formed using a mandrel and/or mold. For example, a mandrel may be formed having protrusions or recesses of the desired size and shape of the pockets 44. The struts 36 may be wound, braided, woven, or otherwise disposed about the mandrel with the cells of the tubular wall aligned with the protrusions or recesses. A sleeve made of, for example, silicone or other polymer material, may be disposed over the mandrel and struts 36. The sleeve may be heated or otherwise molded to the shape of the mandrel to form the coated stent 10 including the pockets 44 between the struts 36. Alternatively, a polymeric material may be spray or dip coated onto the mandrel and struts 36 such that the polymeric material flows over the protrusions and/or into the recesses of the mandrel. In instances that the pockets are formed by protrusions of the mandrel, the pockets may thereafter be inverted to extend radially inward of the tubular wall of the stent 10 subsequent to removing the stent 10 from the mandrel.

Figure 3:
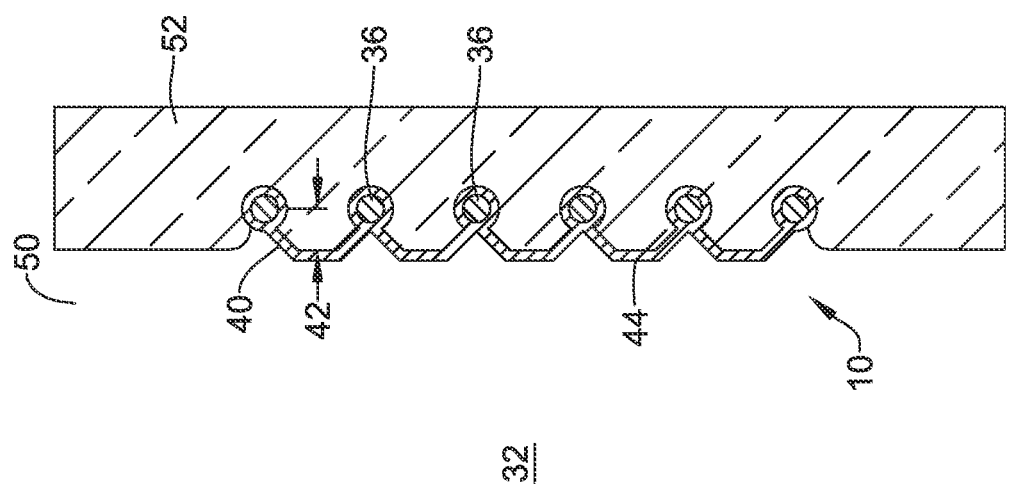
FIG. 3 is a cross-sectional view of the illustrative stent of FIG. 1 disposed within a body lumen.
Figure 3:
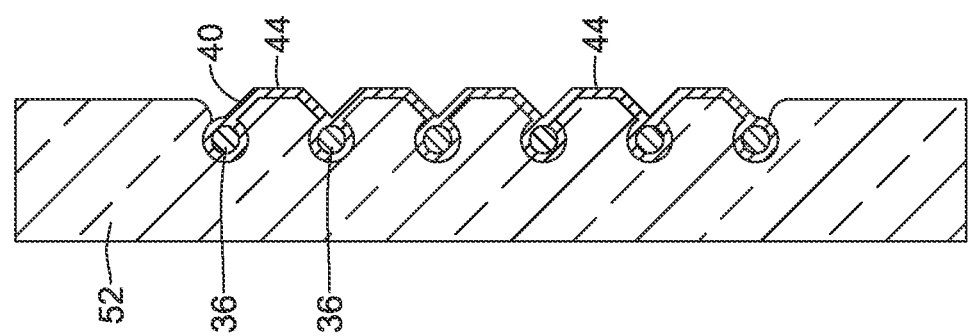

FIG. 3 illustrates a partial cross-sectional view of the illustrative stent 10 of FIG. 1 deployed in a body lumen 50 having a vessel wall 52. It is contemplated that the coating 40 including the pockets 44 may increase frictional forces between the stent 10 and the vessel wall 52 while eliminating or substantially reducing tissue ingrowth around the struts 36 and into the lumen of the stent 10. For example, the coating 40 may be a continuous layer which forms an entirety of the inner surface of the stent 10. In other words, the coating 40 may define an entirety of the inner surface of the lumen extending longitudinally through the stent 10. Thus, the struts 36 may press into the vessel wall 52, but, as the struts 36 are fully covered by the coating 40 and the coating 40 spans the cells of the tubular wall of the stent 10, tissue ingrowth cannot occur around the struts 36 or into the lumen of the stent 10. Said differently, the tissue cannot grow around and surround the struts 36. Further, the tissue of the vessel wall 52 may extend into the void defined by the pockets 44 and radially beyond (e.g., inwardly towards the lumen 32 of the stent 10) the struts 36 which may help reduce migration rates of the stent 10. For example, the pockets 44 may provide textures or contours which increase friction. In contrast, a coating 40 that is generally in the same plane as the struts 36 or at the same circumferential position may provide a generally smooth surface which may have lower frictional forces and increased migration rates.

It is contemplated that the volume of tissue that fills the voids defined by the pockets 44 may be manipulated by changing a volume of the pockets 44. While the pockets 44 are illustrated as having generally uniform dimensions (e.g., are all approximately the same size, shape, and/or volume), the pockets 44 need not all have the same dimensions. For example, some pockets 44 may be larger than others. In some embodiments, one or more of the pockets 44 may include an opening 54, such as, but not limited to, an aperture or slit to allow for limited tissue ingrowth. Limited tissue ingrowth may further reduce migration of the stent 10 while still allowing for the removal of the stent 10 with little difficulty. Alternatively, or additionally, slits or apertures 54 may be provided to allow for a peripheral vessel to drain into the lumen 50 (for example, but not limited to, at the ampulla to allow bile to flow into the duodenum) or to create a drainage channel in the stent 10. In some cases, the physician may create the slits or apertures 54 by cutting or punching through the pockets 44.

FIG. 3A illustrates a partial cross-sectional view of a variation of the illustrative stent 10 of FIG. 1 deployed in a body lumen 50 having a vessel wall 52. In FIG. 3A, it can be seen that the pockets 44 may be formed having a generally arcuate shape, such as a generally spherical shape with a spherically concave radially outward facing surface and a spherically convex radially inwardly facing surface.

Figure 4:
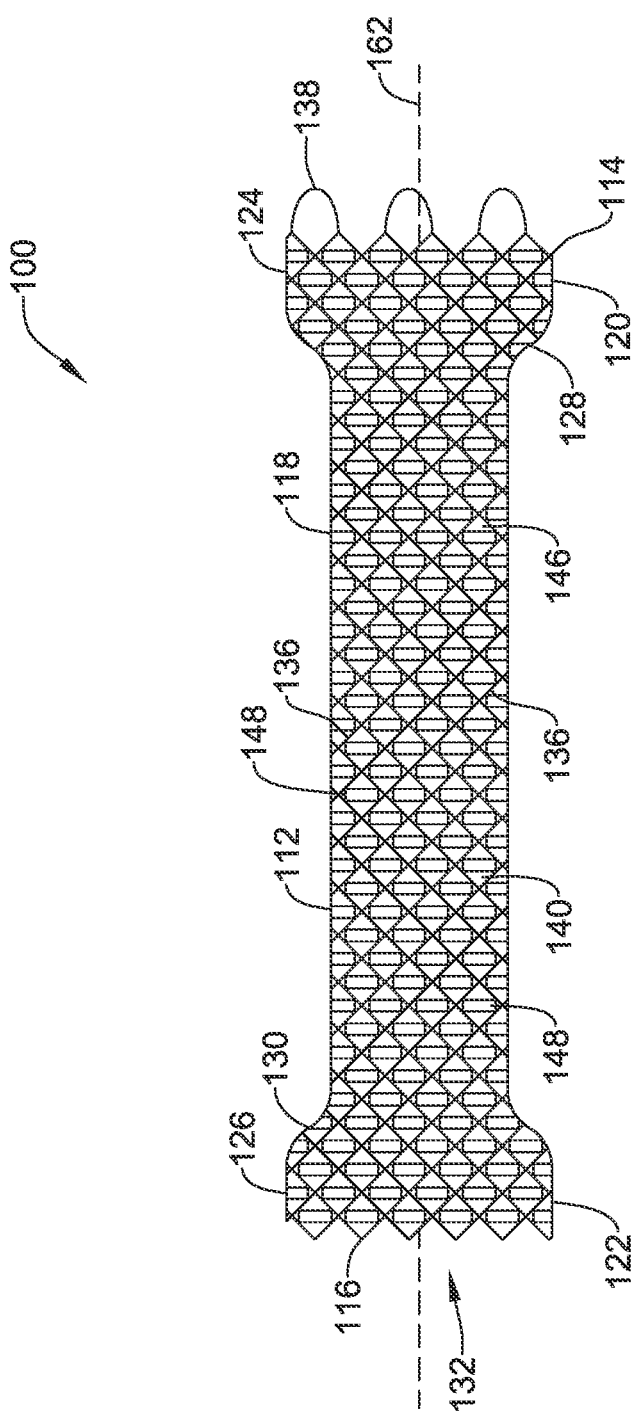
FIG. 4 is a side view of another illustrative stent having an anti-migration system.

FIG. 4 illustrates a side view of another illustrative endoluminal implant 100, such as, but not limited to, a stent. The stent 100 may be similar in form and function to the stent 10 described herein. In some instances, the stent 100 may be formed from an elongated tubular member 112 defining a tubular wall. While the stent 100 is described as generally tubular, it is contemplated that the stent 100 may take any cross-sectional shape desired. The stent 100 may have a first, or proximal end 114, a second, or distal end 116, and an intermediate region 118 disposed between the first end 114 and the second end 116. The stent 100 may include a lumen 132 extending from a first opening adjacent the first end 114 to a second opening adjacent to the second end 116 to allow for the passage of food, fluids, etc.

The stent 100 may be expandable from a first radially collapsed configuration (not explicitly shown) to a second radially expanded configuration. In some cases, the stent 100 may be deployed to a configuration between the collapsed configuration and a fully expanded configuration. The stent 100 may be structured to extend across a stricture and to apply a radially outward pressure to the stricture in a lumen to open the lumen and allow for the passage of foods, fluids, air, etc.

In some embodiments, the proximal end 114 of the stent 100 may include a plurality of loops 138. The loops 138 may be configured to receive a retrieval tether or suture (not explicitly shown) interwoven therethrough, or otherwise passing through one or more of the loops 138. The retrieval suture may be used to collapse and retrieve the stent 100, if so desired. For example, the retrieval suture may be pulled like a drawstring to radially collapse the proximal end 114 of the stent 100 to facilitate removal of the stent 100 from a body lumen.

The stent 100 may have a woven structure, fabricated from a number of filaments or struts 136 forming a tubular wall. In some embodiments, the stent 100 may be knitted or braided with a single filament interwoven with itself and defining open cells 146 extending along a length and around the circumference of the tubular wall of the stent 100. The open cells 146 may each define an opening from an outer surface of the tubular wall to an inner surface of the tubular wall (e.g., through a thickness thereof) that is free from the filaments or struts 136. In other embodiments, the stent 100 may be braided with several filaments or struts interwoven together and defining open cells 146. In another embodiment, the stent 100 may be knitted. In yet another embodiment, the stent 100 may be of a knotted type. In still another embodiment, the stent 100 may be a laser cut tubular member. A laser cut tubular member may have an open and/or closed cell geometry including one or more interconnected monolithic filaments or struts defining open cells 146 therebetween with the open cells 146 extending along a length and around the circumference of the tubular wall. The open cells 146 may each define an opening from an outer surface of the tubular wall to an inner surface of the tubular wall (e.g., through a thickness thereof) that is free from the interconnected monolithic filaments or struts. In some instances, an inner and/or outer surface of the tubular wall of the stent 100 may be entirely, substantially, or partially, covered with a polymeric covering or coating 140, as will be described in more detail herein. The covering or coating 140 may extend across and/or occlude one or more, or a plurality of the cells 146 defined by the struts or filaments 136. The covering or coating may help reduce food impaction and/or tumor or tissue ingrowth. In some cases, the stent 100 may be a self-expanding stent (SES), although this is not required.

In some instances, in the radially expanded configuration, the stent 100 may include a first end region 120 proximate the proximal end 114 and a second end region 122 proximate the second end 116. In some embodiments, the first end region 120 and the second end region 122 may include retention features or anti-migration flared regions 124, 126 having enlarged diameters relative to the intermediate portion 118. The anti-migration flared regions 124, 126, which may be positioned adjacent to the first end 114 and the second end 116 of the stent 10, may be configured to engage an interior portion of the walls of the esophagus or other body lumen. In some embodiments, the retention features, or flared regions 124, 126 may have a larger diameter than the cylindrical intermediate region 118 of the stent 100 to prevent the stent 100 from migrating once placed in the esophagus or other body lumen. It is contemplated that the transition 128, 130 from the cross-sectional area of the intermediate region 118 to the retention features or flared regions 124, 126 may be gradual, sloped, or occur in an abrupt step-wise manner, as desired.

In some embodiments, the first anti-migration flared region 124 may have a first outer diameter and the second anti-migration flared region 126 may have a second outer diameter. In some instances, the first and second outer diameters may be approximately the same, while in other instances, the first and second outer diameters may be different. In some embodiments, the stent 100 may include only one or none of the anti-migration flared regions 124, 126. For example, the first end region 120 may include an anti-migration flare 124 while the second end region 122 may have an outer diameter similar to the intermediate region 118. It is further contemplated that the second end region 122 may include an anti-migration flare 126 while the first end region 120 may have an outer diameter similar to an outer diameter of the intermediate region 118. In some embodiments, the stent 100 may have a uniform outer diameter from the first end 114 to the second end 116. In some embodiments, the outer diameter of the intermediate region 118 may be in the range of about 15 to 25 millimeters. The outer diameter of the anti-migration flares 124, 126 may be in the range of about 20 to 30 millimeters. It is contemplated that the outer diameter of the stent 100 may be varied to suit the desired application.

It is contemplated that the elongated tubular member of the stent 100 can be made from a number of different materials such as, but not limited to, metals, metal alloys, shape memory alloys and/or polymers, as desired, enabling the stent 100 to be expanded into shape when accurately positioned within the body. In some instances, the material may be selected to enable the stent 100 to be removed with relative ease as well. For example, the elongated tubular member of the stent 100 can be formed from alloys such as, but not limited to, nitinol and Elgiloy®. Depending on the material selected for construction, the stent 100 may be self-expanding or require an external force to expand the stent 10. In some embodiments, composite filaments may be used to make the stent 10, which may include, for example, an outer shell or cladding made of nitinol and a core formed of platinum or other radiopaque material. It is further contemplated the elongated tubular member of the stent 100 may be formed from polymers including, but not limited to, polyethylene terephthalate (PET). In some instances, the filaments of the stent 10, or portions thereof, may be bioabsorbable or biodegradable, while in other instances the filaments of the stent 10, or portions thereof, may be biostable.

Figure 5A:
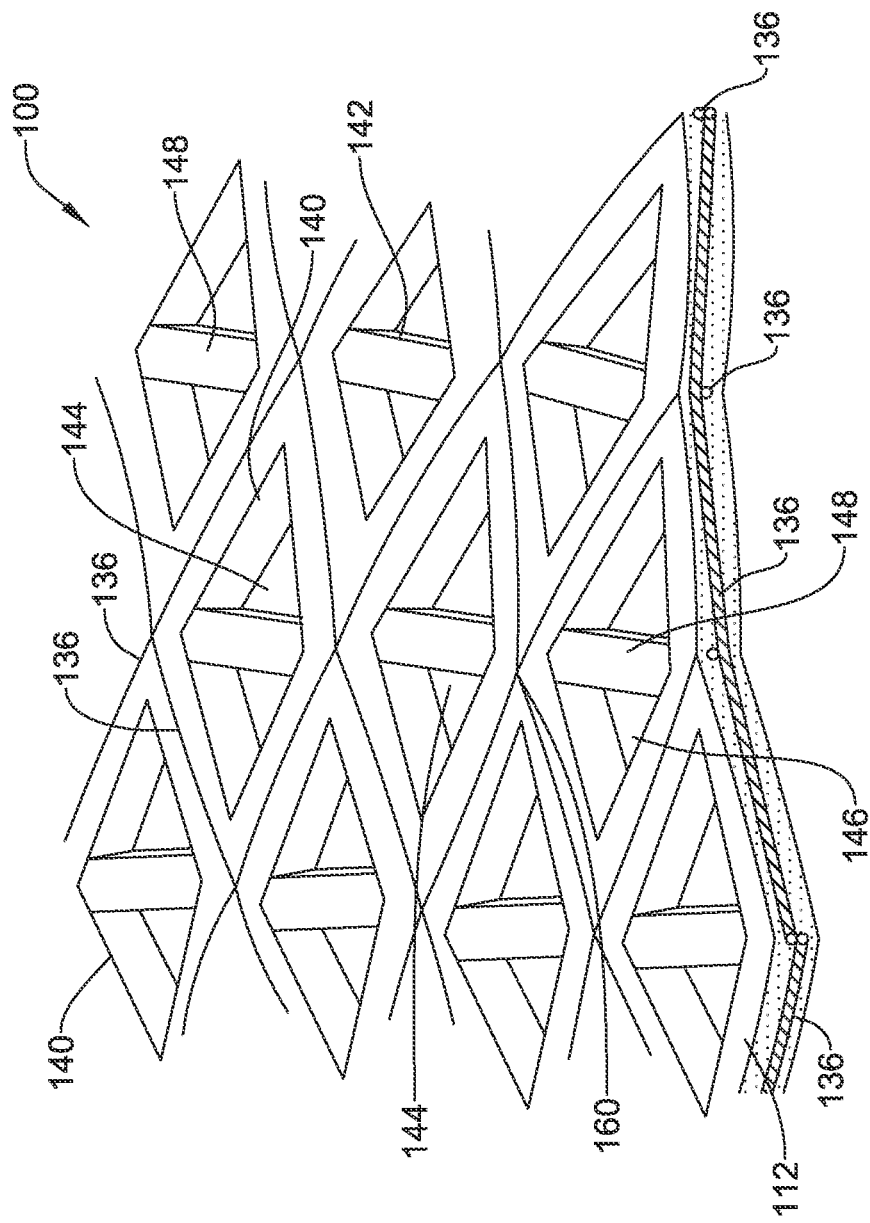
FIG. 5A is a partial perspective view of another illustrative stent.
Figure 5B:
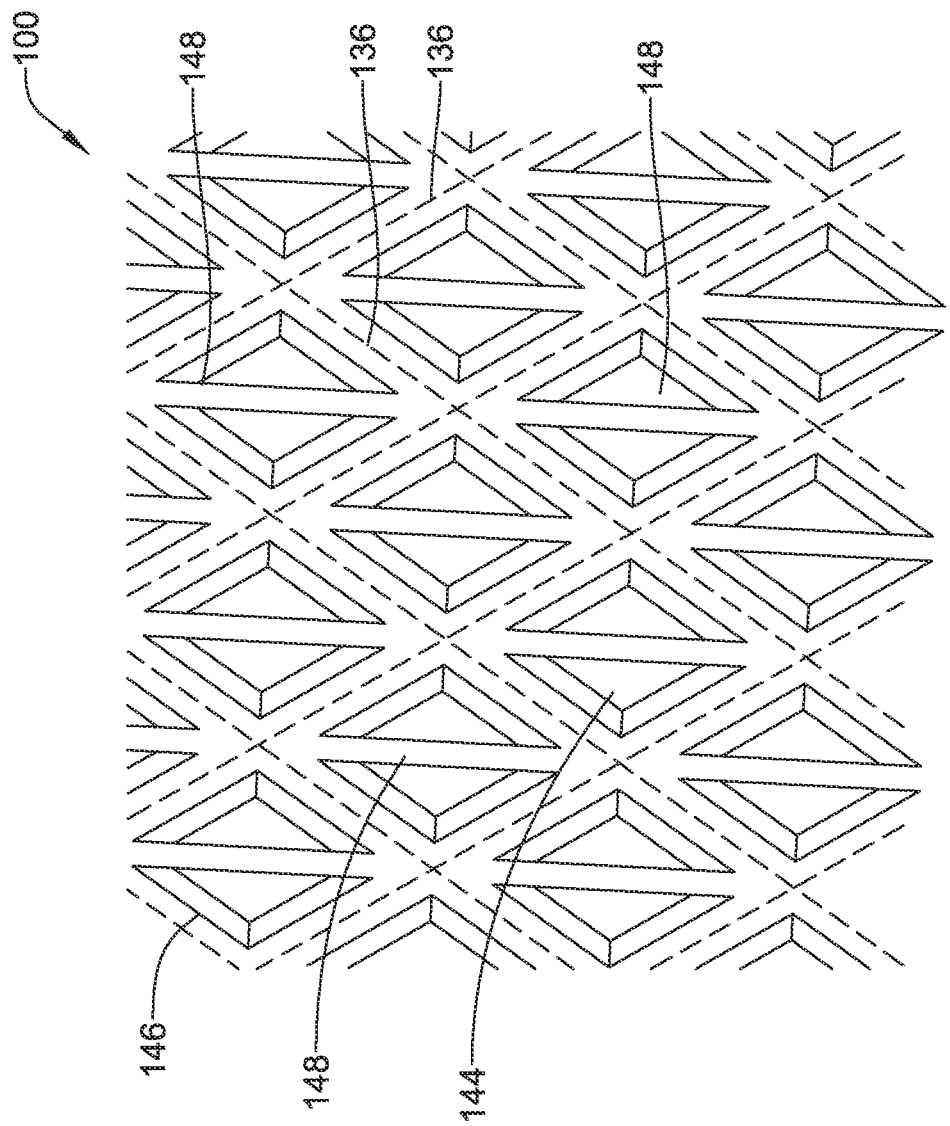
FIG. 5B is a partial side view of the illustrative stent of FIG. 4A.

FIG. 5A illustrates a partial perspective view of the illustrative stent 100 of FIG. 4 and FIG. 5B illustrates a partial side view of the illustrative stent 100 of FIG. 4. As described above, the inner and/or outer surface of the tubular wall of the stent 100 may be entirely, substantially, or partially covered with a polymeric covering or coating 140. The coating 140 may be silicone, polyurethane or other flexible polymeric material. The coating 140 may be applied such that there is an excess of material or a pocket of material 144 extending between the struts 136. For example, instead of extending generally taut in the same plane as the struts 136, the coating 140 may be loose and extend radially inward from the struts 136 for a radial distance or height 42 to form a void. In some instances, the pocket 144 may be generally pyramidal shaped, with four flat converging (e.g., angled) side walls and a flat bottom or base wall. While the pocket 144 is generally illustrated as having a rhombus cross-sectional shape similar to a diamond shape of the cells 146 formed by the struts 136, the pocket 144 may take any shape desired. For instance, in some instances the pocket 144 may have a base wall having a generally arcuate shape, such as a generally spherical shape with a spherically concave radially outward facing surface and a spherically convex radially inwardly facing surface. The pocket 144 may form a void between a radially outward surface (e.g., a base surface) of the pocket 144 and the circumference of the tubular wall of the stent 100 formed by the struts 136.

In some cases, the pocket 144 may be divided or split using a partition or wall 148. It is contemplated that the partition or wall 148 may be formed from the same material as or a different material from the coating 140, as desired. Each partition or wall 148 may extend across the pocket 144 to transect the void formed by the pocket 144. For example, each partition or wall 148 may extend entirely across the void from a first side of the pocket 144 to a second side of the pocket 144 in which it is situated and radially outward from a bottom surface thereof. For example, each partition or wall 148 may extend entirely across the void from a first side wall of the pocket 144 to a second side wall of the pocket 144 in which it is situated and radially outward from a base wall thereof. In other instances, each partition or wall may extend only across a portion of the void and have one or more ends spaced away from the side walls of the pocket 144. The partitions or walls 148 may be formed as a single monolithic structure with the coating 140 and pockets 144. In other embodiments, the partitions or walls 148 may be formed as a separate structure and subsequently secured within the pocket 144 using, for example, heat and/or adhesives. In some cases, the partition or wall 148 may be configured to extend between opposing cross-over points 160 of intersecting struts 136. For instance, in some instances, the partition or wall 148 may extend from a first corner to an opposite corner of a pyramidal shaped pocket 144. This may divide the void defined by the pocket 144 in approximately half. In some cases, the partitions or walls 148 may extend generally orthogonal to a central longitudinal axis 162 (see, for example, FIG. 4) of the stent 100. However, this is not required. In some embodiments, the partitions or walls 148 may extend generally parallel to the central longitudinal axis 162 of the stent 100. In yet other embodiments, the partitions or walls 148 may extend at an oblique angle relative to the central longitudinal axis 162. For example, a first end of the partition or wall 148 may be positioned between two adjacent cross-over points 160 and a second end of the same partition or wall 148 may be positioned between two adjacent cross-over points 160 on an opposite side of the cell 146. Thus, the partition or wall 148 may extend from a first corner to an opposite corner of a pyramidal shaped pocket 144. In some cases, the partitions or walls 148 may be oriented in differing directions. For example, some partitions or walls 148 may extend generally perpendicular to the central longitudinal axis 162, some partitions or walls 148 may extend generally parallel to the central longitudinal axis 162, and/or some partitions or walls 148 may extend at an oblique angle relative to the longitudinal axis 162, or any combination thereof. It is further contemplated that the partition or wall 148 may not divide the pocket 144 uniformly. In some embodiments, one or more pockets 144 may include more than one wall 148, for example.

The partitions or walls 148 may have first and second opposing side surfaces facing first and second divided regions of the void, respectively. The partitions or walls 148 may have a base joined to the base wall of the pocket 144, and an opposite free end extending radially outward therefrom.

In some instances, the pockets 144 and/or partitions or walls 148 may be formed using a mandrel and/or mold. For example, a mandrel may be formed having recesses of the desired size and shape of the pockets 144 with protrusions extending outward from the recesses to form the partitions or walls 148. The struts 136 may be wound, braided, woven, or otherwise disposed about the mandrel with the cells of the tubular wall aligned with the recesses. A sleeve made of, for example, silicone or other polymer material, may be disposed over the mandrel and struts 136. The sleeve may be heated or otherwise molded to the shape of the mandrel to form the coated stent 100 including the pockets 144 and partitions or walls 148 between the struts 136. Alternatively, a polymeric material may be spray or dip coated onto the mandrel and struts 136 such that the polymeric material flows over the protrusions and/or into the recesses of the mandrel.

Figure 6:
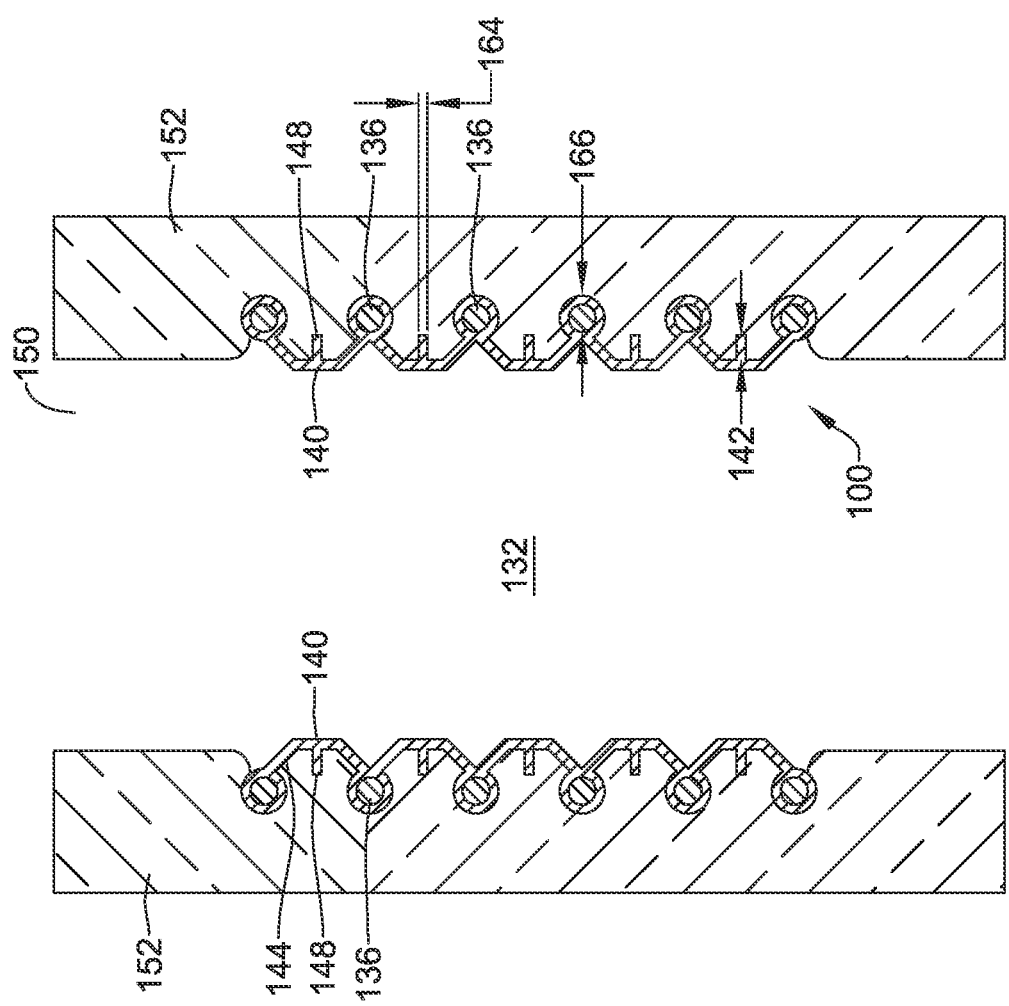
FIG. 6 is a cross-sectional view of the illustrative stent of FIG. 4 disposed within a body lumen.

FIG. 6 illustrates a partial cross-sectional view of the illustrative stent 100 of FIG. 4 deployed in a body lumen 150 having a tissue wall 152. It is contemplated that the coating 140 including the pockets 144 and partitions or walls 148 may increase frictional forces between the stent 100 and the tissue wall 152 while eliminating or substantially reducing tissue ingrowth around the struts 136 and into the lumen of the stent 100. For example, the coating 140 may be a continuous layer which forms an entirety of the inner surface of the stent 100. In other words, the coating 140 may define an entirety of the inner surface of the lumen extending longitudinally through the stent 100. Thus, the struts 136 may press into the tissue wall 152, but, as the struts 136 are fully covered by the coating 140 and the coating spans the cells of the tubular wall of the stent 100, tissue ingrowth cannot occur around the struts 136 or into the lumen of the stent 100. Said differently, the tissue cannot grow around and surround the struts 136. Further, the tissue of the tissue wall 152 may extend into the pockets 144 and, sometimes radially beyond (e.g., inwardly towards the lumen 132 of the stent 100) the struts 136 which may help reduce migration rates of the stent 10. For example, the pockets 144 may provide textures or contours which increase friction. In contrast, a coating 140 that is generally in the same plane as the struts 136 or at the same circumferential position may provide a generally smooth surface which may have lower frictional forces and increased migration rates. It is contemplated that the partitions or walls 148 may increase the surface area of the coating 140 to further increase the friction properties of the stent 100. It is contemplated that width 164 and/or height 142 of the partition or wall 148 may be varied to increase or decrease the surface area of the coating 140. For example, while the stent 100 is generally illustrated as the walls 148 having a height 142 approximately equal to a height of the strut 136 with the coating 140 disposed thereon, the height 142 may be greater than or less than the height of the strut 136 with the coating 140 disposed thereon. It is further contemplated that the partitions or walls 148 each have the same height 142. It is contemplated that the height 142 may vary uniformly, non-uniformly, in a patterned arrangement or eccentrically about the length and/or circumference of the stent 100. While the partition or wall 148 is illustrated as having a generally cubic rectangular shape, other shapes may be used, such as, but not limited, hemispherical, conical, pyramidal, etc.

It is contemplated that the volume of tissue that fills the voids of the pockets 144 may be manipulated by changing a volume of the pockets 144 and/or the size of the walls partitions or 148. While the pockets 144 and partitions or walls 148 are each illustrated as having generally uniform dimensions (e.g., are all approximately the same size, shape, and/or volume), the pockets 144 and/or partitions or walls 148 need not all have the same dimensions. For example, some pockets 144 and/or partitions or walls 148 may be larger than others. In some embodiments, one or more of the pockets 144 may include an opening, such as, but not limited to, an aperture or slit to allow for limited tissue ingrowth. Limited tissue ingrowth may further reduce migration of the stent 100 while still allowing for the removal of the stent 100 with little difficulty. Alternatively, or additionally, slits or apertures may be provided to allow for a peripheral vessel to drain into the lumen 150 or to create a drainage channel in the stent 100. In some cases, the physician may create the slits or apertures by cutting or punching through the pockets 144.

FIG. 6A illustrates a partial cross-sectional view of a variation of the illustrative stent 100 of FIG. 4 deployed in a body lumen 50 having a vessel wall 52. In FIG. 6A, it can be seen that the pockets 144 may be formed having a generally arcuate shape, such as a generally spherical shape with a spherically concave radially outward facing surface and a spherically convex radially inwardly facing surface. The partitions or walls 148 may extend radially outward from the spherically concave outward facing surface.

The stents, delivery systems, and the various components thereof, may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys, nickel-copper alloys, nickel-cobalt-chromium-molybdenum alloys, nickel-molybdenum alloys, other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys; platinum enriched stainless steel; titanium; combinations thereof; and the like; or any other suitable material.

Some examples of suitable polymers for the stents or delivery systems may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

In at least some embodiments, portions or all of the stents or delivery systems may also be doped with, made of, or otherwise include a radiopaque material. Radiopaque materials are generally understood to be materials which are opaque to RF energy in the wavelength range spanning x-ray to gamma-ray (at thicknesses of <0.005"). These materials are capable of producing a relatively dark image on a fluoroscopy screen relative to the light image that non-radiopaque materials such as tissue produce. This relatively bright image aids the user of the stents or delivery systems in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the stents or delivery systems to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A stent, the stent comprising:
   an elongated tubular member comprising at least one strut forming a tubular wall having a plurality of cells extending through a thickness of the tubular wall, the elongated tubular member configured to move between a radially collapsed configuration and a radially expanded configuration;
   a coating disposed on the elongated tubular member and spanning the plurality of cells, the coating forming a pocket within at least some of the plurality of cells and extending radially inward of the tubular wall to define a void; and
   a partition positioned within at least some of the pockets, each partition extending radially outward from a bottom surface of the pocket and transecting the void;
   wherein the partitions have a first end attached to a first side wall of the pocket and a second end attached to a second side wall of the pocket;
   wherein the bottom surface of the pocket faces radially outward and is disposed radially inward of the tubular wall.

2. The stent of claim 1, wherein at least some of the partitions extend generally perpendicular to a central longitudinal axis of the elongated tubular member.

3. The stent of claim 1, wherein at least some of the partitions extend generally parallel to a central longitudinal axis of the elongated tubular member.

4. The stent of claim 1, wherein at least some of the partitions extend at an oblique angle relative to a central longitudinal axis of the elongated tubular member.

5. The stent of claim 1, wherein a height of the partitions is approximately equal to a height of the at least one strut having the coating disposed thereon.

6. The stent of claim 1, wherein the at least one strut forms a plurality of cross-over points.

7. The stent of claim 6, wherein at least some of the partitions extend between adjacent cross-over points.

8. The stent of claim 1, wherein at least one pocket includes two or more partitions.

9. The stent of claim 1, wherein the coating defines an entirety of a surface of a lumen extending longitudinally through the stent.

10. The stent of claim 1, wherein at least some of the pockets include an aperture formed therethrough.

11. The stent of claim 1, wherein the coating and the partitions are formed as a single monolithic structure.

12. A stent, the stent comprising:
   an elongated tubular member comprising at least one interwoven filament forming a tubular wall, the at least one interwoven filament forming a plurality of cross-over points and defining a plurality of cells therebetween extending through a thickness of the tubular wall, the elongated tubular member configured to move between a radially collapsed configuration and a radially expanded configuration;
   a polymer coating disposed on the elongated tubular member, the coating forming a pocket within at least some of the plurality of cells and extending radially inward of the tubular wall to define a void; and a partition formed within at least some of the pockets, each partition extending radially outward from a bottom surface of the pocket and transecting the void between opposing cross-over points of the at least one strut forming the cell in which the pocket is positioned;

wherein the partitions have a first end attached to a first side wall of the pocket and a second end attached to a second side wall of the pocket;

wherein the bottom surface of the pocket is a radially outward facing surface of the coating that is spaced apart radially inwardly of an inner surface of the tubular wall.

13. The stent of claim 12, wherein at least some of the partitions extend generally perpendicular to a central longitudinal axis of the elongated tubular member.

14. The stent of claim 12, wherein at least some of the partitions extend generally parallel to a central longitudinal axis of the elongated tubular member.

15. The stent of claim 12, wherein the coating defines an entirety of a surface of a lumen extending longitudinally through the stent.

16. The stent of claim 12, wherein the coating and the partitions are formed as a single monolithic structure.

17. The stent of claim 12, wherein a radial outermost extent of the partitions is located flush with or radially inward of an outer surface of the tubular wall.

18. A stent, the stent comprising:

an elongated tubular member comprising at least one strut forming a tubular wall having a plurality of cells extending through a thickness of the tubular wall, the elongated tubular member configured to move between a radially collapsed configuration and a radially expanded configuration; and a coating disposed on the elongated tubular member and spanning the plurality of cells, the coating forming a pocket within at least some of the plurality of cells and extending radially inward of the tubular wall to define a void;

wherein the pockets are truncated pyramidal shaped, with four flat converging side walls intersecting a radially outward facing surface at a flat base of each pocket;

wherein the radially outward facing surface at the base of each pocket is spaced apart radially inwardly of a radially innermost extent of the tubular wall; and further comprising a partition positioned within at least some of the pockets, each partition extending radially outward from the radially outward facing surface at the base of its respective pocket and transecting the void, wherein the partitions have a first end attached to a first side wall of the pocket and a second end attached to a second side wall of the pocket.

* * * * *